Figure 1:
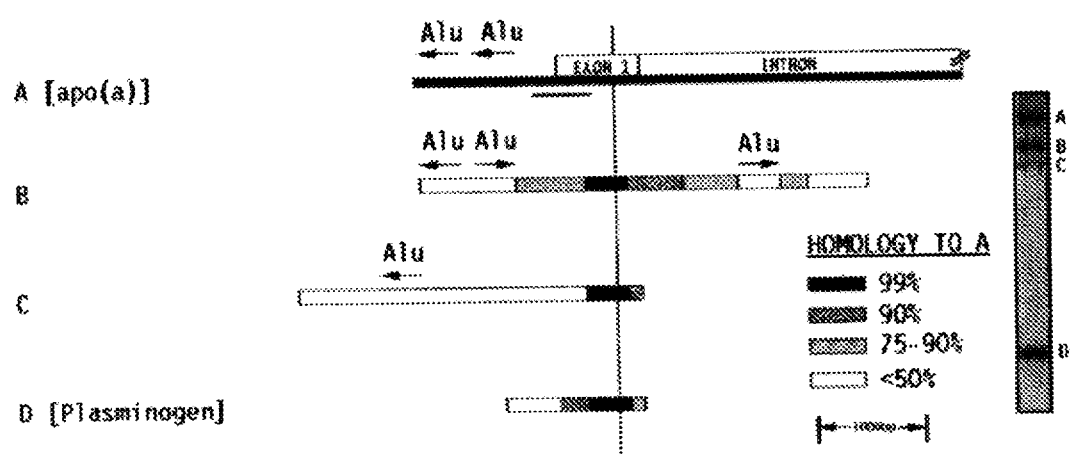

United States Patent [19]
Lawn

[11] Patent Number: 5,721,138
[45] Date of Patent: Feb. 24, 1998

[54] APOLIPOPROTEIN(A) PROMOTER AND REGULATORY SEQUENCE CONSTRUCTS AND METHODS OF USE

[75] Inventor: Richard Mark Lawn, San Francisco, Calif.

[73] Assignee: Sandford University, Stanford, Calif.

[21] Appl. No.: 441,370

[22] Filed: May 15, 1995

Related U.S. Application Data

[63] Continuation of Ser. No. 991,849, Dec. 15, 1992, abandoned.

[51] Int. Cl.$^6$ ............................ C12N 5/00; C12N 15/00; C07H 21/04
[52] U.S. Cl. .................. 435/325; 435/320.1; 536/23.2; 536/24.1; 935/6; 935/22; 935/70
[58] Field of Search ........................... 435/320.1, 240.2; 800/2, DIG. 1; 536/24.1, 23.2; 935/6, 22, 70

[56] References Cited

U.S. PATENT DOCUMENTS 4,935,363 6/1990 Brown et al. ........................ 435/172.3

OTHER PUBLICATIONS

Malinowski et al., 1984, "Characterization of a Complementary Deoxyribonucleic Acid Coding for Human and Bovine Plasminogen" *Biochem.* 23:4243–4250.

Brinster et al., 1985, "Factors Affecting the Efficiency of Introducing Foreign DNA Into Mice by Microinjecting Eggs" *Proc. Natl. Acad. Sci. USA* 82:4438–4442.

Palmiter et al., 1986, "Germ–Line Transformation of Mice," *Ann. Rev. Genet.* 20:465–99.

Rhoads et al., 1986, "Lp(a) Lipoprotein as a Risk Factor for Myocardial Infarction" *JAMA* 256:2540–2544.

Forsgren et al., 1987, "Molecular Cloning and Characterization of a Full–Length cDNA Clone for Human Pasminogen" *FEBS Letters* 213:254–260.

Scangos et al., 1987, "Gene Transfer Into Mice," *Advances in Genetics* 24:285–322.

Durrington et al., 1988, "Apolipoproteins(a), AI, and B and Parental History in Men with Early Onset Ischaemic Heart Disease" *Lancet* 1070–1073.

Baribault et al., 1989, "Embryonic Stem Cell Culture and Gene Targeting in Transgenic Mice," *Mol. Biol. Med.* 6:481–492.

Gordon, Jon W., 1990, "Transgenic Animals," *Laboratory Animals* 19:27–35.

Hattori et al., 1990, "Acute–Phase Reaction Induces a Specific Complex Between Hepatic Nuclear Proteins and the Interleukin 6 Response Element of the Rat $\alpha_2$–Macroglobulin Gene" *Proc. Natl. Acad. Sci. USA* 87:2364–2368.

Koschinsky et al., 1990, "Apolipoprotein(a) Size Heterogeneity Is Related to Variable Number of Repeat Sequences in Its mRNA" *Biochem.* 29:640–644.

Malgaretti et al., 1990, "Definition of the Transcription Initiation Site of Human Plasminogen Gene in Liver and Non Hepatic Cell Lines" *Biochem. Biophys. Res. Comm.* 173:1013–1018.

Peterson et al., 1990, "Characterization of the Gene for Human Plasminogen, a Key Proenzyme in the Fibrinolytic System" *J. Biol. Chem.* 265:6104–6111.

Ausabel et al., 1991, *Current Protocols in Molecular Biology*, pp. 4.8.1–4.8.3.

(List continued on next page.)

*Primary Examiner*—Bruce R. Campell
*Attorney, Agent, or Firm*—Pennie & Edmonds LLP

[57] ABSTRACT

An apo(a) gene 5'-regulatory region upstream from position –208 from the translation initiation site is provided. Also included are expression constructs, vectors, translated cells, and transgenic animals comprising the regulatory region, and methods for determining expression levels and for screening for compounds which control expression.

36 Claims, 5 Drawing Sheets

OTHER PUBLICATIONS

Beal et al., 1991, "Second Structural Motif for Recognition of DNA by Oligonucleotide–Directed Triple–Helix Formation" *Science* 251:1360–1363.

Chambaz et al., 1991, "Promoter Elements and Factors Required for Hepatic Transcription of the Human ApoA–II Gene" *J. Biol. Chem.* 266:11676–11685.

Chastain et al., 1991, "Poly(rA) binds poly(rG)–poly(rC) to form a triple helix" *Nucleic Acids Res.* 20:315–318.

Ichinose et al., 1991, "Two Types of Abnormal Genes for Plasminogen in Families With a Predisposition for Thrombosis" *Proc. Natl. Acad. Sci. USA* 88:115–119.

Koschinsky et al., 1991, "Apolipoprotein(a): Expression and Characterization of a Recombinant Form of the Protein in Mammalian Cells" *Biochem.* 30:5044–5051.

Lawn, R. M., 1991, "The structure and evolution of apolipoprotein(a)" pp. 209–211. In: Scanu AM, moderator, Lipoprotein(a) and Atherosclerosis, *Ann. Inter. Med.* 115:209–218.

Miyazawa et al., 1991, "Structural Organization and the Transcription Initiation Site of the Human Hepatocyte Growth Factor Gene" *Biochem.* 30:9170–9176.

Orson et al., 1991, "Oligonucleotide inhibition of IL2RAα mRNA transcription by promoter region collinear triplex formation in lymphocytes" *Nucleic Acids Res.* 19:3435–3441.

Papazafiri et al., 1991, "Promoter Elements and Factors Involved in Hepatic Transcription of the Human Apo–A–I Gene Positive and Negative Regulators Bind to Overlapping Sites" *J. Biol. Chem.* 266:5790–5797.

Bischoff et al., 1992, "A 17.6 kbp region Located Upstream of the Rabbit WAP Gene Directs High Level Expression of a Functional Human Protein Variant in Transgenic Mouse Milk," *FEBS Letter* 305(3):265–268.

Chiesa et al., 1992, "Reconstitution of Lipoprotein(a) by Infusion of Human Low Density Lipoprotein into Transgenic Mice Expressing Human Apolipoprotein(a)" *J. Biol. Chem.* 267:24369–24374.

Janne et al., 1992, "Transgenic Animals as Bioproducers of Therapeutic Proteins," *Annals of Medicine* 24:273–280.

Ichinose, Akitada, 1992, "Multiple Members of the Plasminogen–Apolipoprotein(a) Gene Family Associated with Thrombosis" *Biochem.* 31:3113–3118.

Liggitt et al., 1992, "Transgenic Animals in the Evaluation of Compound Efficacy and Toxicity: Will They Be As Useful As They Are Novel?," *Xenobiotica* 22:1043–1054.

Schedl et al., 1992, "Transgenic Mice Generated by Pronuclear Injection of a Yeast Artificial Chromosome," *Nucleic Acids Res.* 20(12):3073–3077.

Schultz et al., 1992, "Expression of Human Apolipoprotein A–II and Its Effect on High Density Lipoproteins in Transgenic Mice," *J. Biol. Chem.* 267(3):21630–21636.

RR Franks et al (1988) Genes and Development 2:1–12.

Lavenu et al (1994) Oncogene 9: 527–536.

SY Chung et al (1994) Molecular and Cellular Differentiation 2: 61–81.

M Cohen–Tannoudji et al (1992) Molecular Reproduction and Development 33: 149–159.

JW McLean et al (1987) Nature 330:132–137.

GI Liou et al (1990) J Biol Chem 265(15):8373–8376.

LJ Maher III et al (1989) Science 245: 725–730.

N Malgaretti et al (1992) Proc Natl Acad Sci USA 89:11584–11588.

G Audesirk et al (1986) Biology. Life on Earth. pp. 397–398.

FIG. 3-1

```
                                                               GAATTCATTTGCGGAAAGATTGATACTATGCTTTATTTAT
-1400  TTTATTTATTTATTTATTTATTTGAGACTCTCACCCGGTTGAAGTGCACTGACGTGATTTTGGCTCACTGCAACTTCCACCTCCTGGGTC
                       IL-6
-1300  AAGTGAATACTCCAGCCTCCCTAGTAG[CTGGGA]TTACAGGTGCCCACCACCACGGCTGGCTAATTTTTGTATTTTAGTAGAGATGGGGTTTCACCACAT
                                                  IL-6                          LF-A1
-1200  TGGCCTGGCTGGTCTCAAACTCCTGACCTGTGATCCACCTGTCTTGGCCTCCCAAAGTG[CTGGGA]TTACAGAGT[TGAGCCA]CCGCACTGACCCCTCTGT
                                                                                          * CEBP
-1100  TTTATTTTTAAAAATATTTATTTATTTAAGCCACAACTACTAGAATAGGAAGGATTGATATTTTATTAATTTATTGGTATTTATTATTTTTT
-1000  TCTTTCCTGAGACATTCTTGCTCTGTCACCCAGGCTGGAGTGCAGTGGCACATTCTTGGCTCACTGCAACCTCCATCTCCTGTTCGA[GCAAT]TCTAGT
                                                                                   IL-6
-900   GCCTCAGCCTACTTAGTAG[CTGGGA]TGACTGGCATGGCCCTCCACACCCAGCTAATTTTTTGTATTTTTGTAGAGACAGGGTTTTGGCATGTTGCCAGGC
-800   TTGTCTCAAACTCCTGGCCTCAAGTGATCCATCTGCCGTGGCCTCCCAAAATG[CTGGGA]TTATAGGCATGAGCCACCACCCCCTCCTGGAAGGATTGATA
-700   TCTTATAACATAATTTATAATTACAGAAAACATGTGAGTTCACTAGGAATAATAAAGATTTTCACTTATGTGTCATTTCGG
-600   CACAGTTTGGTATAGGGATGTGGAGATGTTAACATTTATACCTAGCTTGCTCGTAAACTAAGACCTGAAAGGGTTGTGTCTATCAGTCTGCACCCCTGGGTA
-500   GCGACACAACCTCGGGAAGGCCTCAGCCCCCCTCCTGTACAGCACTGCTGTTGGAAAGTTGAGGGAGGCTATGATGTGCAGCACTTGGCAGAGGGTC
```

FIG. 3-2

```
-400  TGGTCATGGAAGTTACCAGCAAATATGAGCTACTTTTATGATTTTATTTTATCCAAAAGAAGAGAATGAAAGAAGAGGGGAGGAAACAAGACTAATCAG
                                                                    IL-6                           IL-6RC
-300  GAAAGATGAAGGTCTAGGGG[GAGGGGAA]GAGTAAGGAGACATAAAG[GCAAT]GTGGAGCAGCTGAGGGGGAAATGG[CTTTCACCA]CTTCCCAGCATCTA
        CEBP-RC              IL-6                   CEBP                                                    HNF-1α
-200  TTGAC[ATTG]CACTCT[CAAA]ATTT[TATAA]GACTCTATATTCAAGGTAATGT[TTGAACC]CTGCTGAGCCAGTGGCATGGGTCTCTGA[GAGAATCATTAAG]T
                                                  LF-A1
                                                                                    IL-6
-100  TAATTTGACTATCTGGTTGTGTGGTGCGTTACTCTCATGTAAGTCAACAACGTC[TGGGA]TTGGGACACACTTCTGGGCACTGCTGCCAGTCCCAAA
      ATGAACACATAAGGAAGTGGTTCTCTACTTCTTTTATTTCTGAAATCAGGTAAGACATAGTTTTTTAAATTATAAGAATTATTTTTTCTCCACAATGT
      Met
 101  ATGGAACACATAAGGAAGTGGTTCTCTACTTCTTTTATTTCTGAAATCAGGTAAGACATAGTTTTTTAAATTATAAGAATTATTTTTTCTCCACAATGT
 201  AGTAAAAATACATGCCATGGCTTTATGTGCAATTCATTAATTTTGATTCATGAAATCTTGTATATGATTGAAAAATTCTTCC
 301  AAAAATTAGTTAATTTCCCGTGAAAAAATGGCAGAAAATAATGGTTGATTTTCTAATCTAAAGAGTGTGCCTAC
 401  ATGATGGCCAGTCTGGCTGAAGACTGTCACGGTGCTGGAATGAACAATGCCATTGTCAGCTCTTCGCTTGGTCTCTCAGTTTCATTATTATATC
 501  ATCTCTGTTCAGGTGCCATGCCCCTCACTAGCAAGTTGAAACAATGAAAATAACTCTTTGGTTCCTTGACCTGTTCATGGAGTGGGACT
 601  CAGCATTTCTCTCTTGTTATGGCCTGAGTAAGGCTTTCCATCGGTATACATTTGCTTCTTATCCCTGGAGAAATTATACACATCCATTTGCCAGATGAT
 701  ATACACATATAATGATTCAACAAATACTCAGGGTATTGTTGAGTGGGTTAGGTCCCACATTTTATACATCCCCATTTTATACATAGTGCATCCCATTTT
 801  TGTGAATGTAAGTGTGTGTCCTTGTCATGTCTTACAAATACTAGCTTCATGTGGTAGGGTAGCATAGTCATCCCATTTATAAACAAAGAAATCTA
 901  GACTTAGGAAAATCATGTTATTGTCTCGTGACCAAATTCCCAAATCAAGGATTTAAGCAACTGGATTTCCAAGAGAGTCAGGTAATTGTTGCCACTGCAGA
1001  CTCTTCTCACTTTTCATCTTGTTCCAACATTTGAAAAAAATAAGGAAAGAAAGTGATTGATTTTAGGGAAGAAAATGAGCAGTCCTGCCGTACCACTTCCACTT
```

APOLIPOPROTEIN(A) PROMOTER AND REGULATORY SEQUENCE CONSTRUCTS AND METHODS OF USE

This application is a continuation application of U.S. application Ser. No. 07/991,849, filed Dec. 15, 1992, abandoned, which is incorporated herein by reference in its entirety.

1. INTRODUCTION

The field of the invention pertains to 5' promoter and regulatory element sequences which control expression of apolipoprotein(a); and to constructs and vectors comprising apolipoprotein(a) regulatory sequences operatively linked to heterologous sequences.

2. BACKGROUND OF THE INVENTION

Lipoprotein(a) [Lp(a)] is a variant lipoprotein which has been shown to play a role in development of atherosclerosis. Because atherosclerosis is the leading cause of death in the United States, interest in the structure and function of Lp(a) has greatly increased in recent years. Epidemiological studies have shown a population-attributable risk of 28% for suffering myocardial infarction before sixty years of age in those men having an Lp(a) concentration in the top quartile of the population distribution (Rhoads et al., *JAMA* (1986) 256:2540–4). A study conducted in England found that nearly all instances of familial premature coronary heart disease occurring in the absence of classical hyperlipidemias were associated with high Lp(a) levels (Durrington et al., *Lancet* 1988:1070–3).

2.1 Composition of LP(a) and LDL

Lp(a) is known to constitute a cholesteryl-ester rich low density lipoprotein (LDL)-like particle which closely resembles LDL in content of cholesterol, phospholipid, and apolipoprotein B-100 (apoB). ApoB is the ligand for the LDL receptor. Binding of ApoB to the LDL receptor provides an uptake mechanism for moving LDL into cells, where it provides cholesterol needed for membrane and steroid synthesis. Like LDL, Lp(a) consists of a core of cholesteryl esters and triglycerides, and a surface layer of phospholipids and free cholesterol. In both LDL and Lp(a), the single hydrophobic molecule of apoB is arranged primarily beneath or near the surface of the particle.

Lp(a) is distinguished from LDL by the presence of an additional apolipoprotein known as apo(a), a glycoprotein which is bound to apoB through a disulfide linkage. Unlike the predominantly hydrophobic apoB, apo(a) is a hydrophilic glycoprotein. The disulfide linkage between apoB and apo(a) occurs on a hydrophilic loop of apoB which extends into the aqueous medium surrounding the particle.

2.2 Sequence of Apo(a) and the Apo(a) Gene

Recent studies have provided sequence information about the apo(a) protein and the coding region of the apo(a) gene. Apo(a) comprises a variable number of kringle domains linked to a C-terminal protease domain. The protein and nucleotide sequences of apo(a) are strikingly homologous to the sequences of certain domains of the clotting factor protein plasminogen. Mature plasminogen consists of five distinct kringle domains, numbered 1–5 starting from the N-terminus, and a C-terminal protease domain related to the serine protease trypsin. The five kringles of plasminogen share about 50% sequence identity with one another. They bind plasminogen to its fibrin substrate and to specific inhibitory proteins.

The N-terminal kringles of apo(a) comprise repeating domains most closely related to kringle-4 of plasminogen. The number of copies of the kringle-4-like domain varies dramatically among human alleles. Within the general population, the number of repeated kringle-4 domains appears to range from 15 to 40. This genetic diversity is reflected in the molecular weight variation of mature apo(a), which ranges from 300 to 800 kD (Koschinsky et al., *Biochem.* (1990) 29: 640–4). In one sequenced cDNA clone, 22 tandem exact repeats and 15 modified repeats of kringle-4 were found. These copies exhibit from 75% to 85% nucleotide identity to plasminogen kringle-4.

Moreover, an even greater sequence identity was observed between kringle-5 of plasminogen and a single copy of an apo(a) kringle, located C-terminal to the kringle-4-like repeated domains of apo(a). The kringle-5-like domain exhibits 91% nucleotide sequence identity with kringle-5 of plasminogen.

Immediately C-terminal to the kringle-5-like domain is a protease domain which exhibits 94% nucleotide and 88% amino acid sequence identity with the protease domain of plasminogen.

Even more pronounced homology is found at the 5' end of the transcribed gene message. Plasminogen and apo(a) contain 5'-untranslated sequences which share 98% sequence homology, followed by a signal peptide sequence which is 100% identical.

2.3 Regulation of Serum Lp(a) Levels

Covalent linkage of the apo(a) moiety to apoB is believed to inhibit uptake of Lp(a) by the LDL receptor. Such uptake is the primary means for clearing LDL from plasma. The diminished cellular uptake observed for Lp(a) suggests that regulation of Lp(a) serum levels may depend more upon control of the rate of Lp(a) synthesis than upon the rate of metabolism.

Although elevated Lp(a) levels pose a significantly increased risk of premature coronary heart disease, no practicable method for lowering the serum concentration of Lp(a) is presently known. Unlike LDL levels, Lp(a) serum concentration appears to be insensitive to dietary or exercise regimens. Instead, the Lp(a) level apparently is genetically determined, and remains relatively constant throughout the lifetime of a given individual. Elevated Lp(a) levels appear to be inherited as a dominant trait under single-locus control.

Furthermore, with the exception of nicotinic acid, all drugs tested to date have failed to reduce Lp(a) concentrations. Even HMG-CoA reductase inhibitors, which dramatically reduce LDL concentration by inhibiting cholesterol synthesis, fail to lower the concentration of Lp(a).

Consequently a need exists for improved methods and compositions for reducing the serum concentration of Lp(a). In particular, lower Lp(a) levels might be obtained by limiting the expression of its unique component, apo(a). However, at present very little is known about the physiological or hormonal control of apo(a) expression.

2.4 5' Regulatory Elements of Mammalian Genes

One approach to deciphering the regulation of apo(a) expression is to isolate the 5' genomic regulatory elements. The upstream regulatory sequences of numerous mammalian genes have been shown to contain regulatory "elements", i.e., relatively short nucleotide sequences which either enhance or inhibit transcription of the proximal coding region. Most regulatory elements are believed to function by binding particular regulatory proteins which can selectively associate with a specific DNA sequence. These DNA-binding regulatory proteins may provide for tissue-specific developmentally and hormonally regulated gene expression.

Certain DNA-binding regulatory proteins are known to be receptors for particular hormones, such as glucocorticoid, estrogen, and thyroid hormones. Each hormone receptor targets a distinct DNA site or response element. In general, binding of the hormone to the receptor protein alters the affinity of the receptor protein for its cognate DNA response element. In the case of lipid-soluble hormone receptors, binding of the hormone-receptor complex to its DNA response element stimulates transcription, i.e., exhibits positive regulation.

Other examples of positive regulatory elements are provided by transcription enhancing factors activated by hormones which bind to cell surface receptors, such as interferon α. Binding of interferon α to its cell surface receptor leads to the association of three cytoplasmic proteins, each of which is inactive by itself, to form the active interferon α-stimulated factor. The active factor is translocated to the cell nucleus and in turn stimulates transcription of those genes having a cognate DNA binding site.

In addition to these examples of positive or up regulation of transcription, regulatory elements which confer suppression of transcription also have been identified in some mammalian genes. For example, a suppressive sterol regulatory element (SRE) has been found in the upstream region of the LDL receptor gene (U.S. Pat. No. 4,935,363 to Brown et al.). Frequently both positive and negative regulatory elements occur within the same upstream regulatory region, as has been reported for the gene for apoA-I. ApoA-I is a principal apoprotein component of high density lipoproteins (HDL) (Papazafiri et al., *J Biol. Chem.* (1991) 266:5790–7).

2.5 Anticipated Difficulties in Isolating Apo(a) 5' Regulatory Elements

If a comparable understanding of the regulatory elements responsible for positive and negative control of transcription of apo(a) could be obtained, a rational search for therapeutics might be conducted. However, although the coding regions of the apo(a) gene have been cloned and sequenced, the regulatory regions thus far have not been isolated or characterized. At least in part, the failure to identify clones containing the apo(a) 5'-regulatory region may reflect difficulties arising from the unusually high degree of homology between apo(a) and plasminogen. The extreme homology between the 5' portions of the plasminogen and apo(a) genes is particularly significant because the 5' transcribed region is immediately adjacent to the upstream regulatory region. Therefore, probes directed to the 5'-transcribed region would be especially useful for screening a genomic library to identify the apo(a) regulatory sequences. The extensive identity between apo(a) and plasminogen nucleotide sequences indicates that such probes would be expected to cross-react with the plasminogen gene even under stringent conditions of hybridization.

To further complicate identification of the apo(a) regulatory region, recent studies by Ichinose, *Biochemistry* (1992) 31:3113, and Ichinose et al., *Proc. Natl. Acad. Sci. USA* (1991) 88:115, have demonstrated that plasminogen and apo(a) are members of a multiple gene family. At least two distinct genomic clones coding for apo(a) were reported, although one or both could be pseudogenes. Furthermore, three other plasminogen-related genes (PRGs) or pseudogenes having high homology to parts of the plasminogen and apo(a) coding sequences also were observed. Finally, hepatocyte growth factor has been found to constitute yet another member of the plasminogen-apo(a) gene family (Miyazawa et al., *Biochemistry* (1991) 30:9170–6).

Not surprisingly in view of the presence of this extensive family of related genes, a cDNA probe comprising a plasminogen kringle-4 sequence identified a large number of genomic fragments on a Southern blot (Ichinose, supra, pp. 3113–4 and FIG. 1 therein).

Despite these anticipated difficulties in identifying genomic regulatory regions of apo(a), the search for such regulatory regions holds great promise for devising physiological or pharmacological interventions in the level of expression of apo(a). Such intervention would be extremely useful in preventing premature coronary heart disease.

3. BRIEF DESCRIPTION OF THE DRAWINGS

FIG. 1 shows homologous regions from the 5'ends of members of the apolipoprotein(a)/plasminogen gene family. On the right is seen a blot hybridization of human genomic DNA digested with EcoRI, electrophoresed, transferred and probed with PCR-A, a 483 bp fragment from the 5' end of the plasminogen gene. The hybridizing fragments are 4.8, 3.6, 3.1 and 1.2 kb in length. Local regions of DNA sequence identity to the 4.8 kb A fragment are shown. The fragments are shown aligned to the ATG translation initiation codon. Exon one begins at the transcription start site and ends at a splice donor sequence shared by all four fragments. The location of repetitious "Alu" sequences and their orientation is shown. The D fragment size class consists of three or more non-allelic species containing over 95% sequence identity throughout their length, one of which corresponds to the plasminogen gene.

Figure 2:
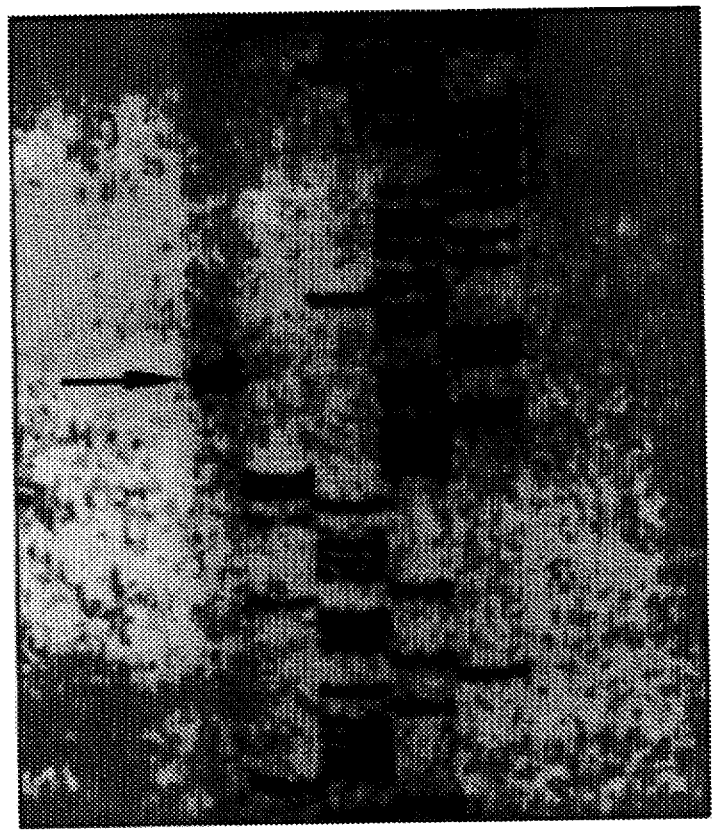

FIG. 2 is a map of the transcription start site (arrow) of apolipoprotein (a). An antisense primer complementary to nucleotides 60–72 bp downstream of the ATG of human apo(a) cDNA (McLean et al., *Nature*(1987) 330:132–137) was annealed to 20μg of human liver poly (A+) RNA and extended with reverse transcriptase as described in Ausabel et al., *Current Protocols in Molecular Biology* (1991) pp. 4.8.1–4.8.3. A DNA sequence ladder is included as a size marker.

FIG. 3 (SEQ. ID NO: 1) shows the sequence characteristics of the 5' region of the human apolipoprotein(a) gene. Partial sequence is presented of the EcoRI "A" fragment; the complete 4798 bp sequence is available from GenBank. The first nucleotide of the translation initiation codon is numbered one. Sequences resembling CAAT, TATAA boxes and other consensus sequences for transcription regulatory elements are boxed, and exon one is underlined. The "A2" allele isolated from individual with low plasma and reporter gene expression of apo(a) (see FIG. 4 and text) has two sequence differences with the above: an insert of TTTTA indicated by v and a G to A substitution indicated by *.

Figure 4:
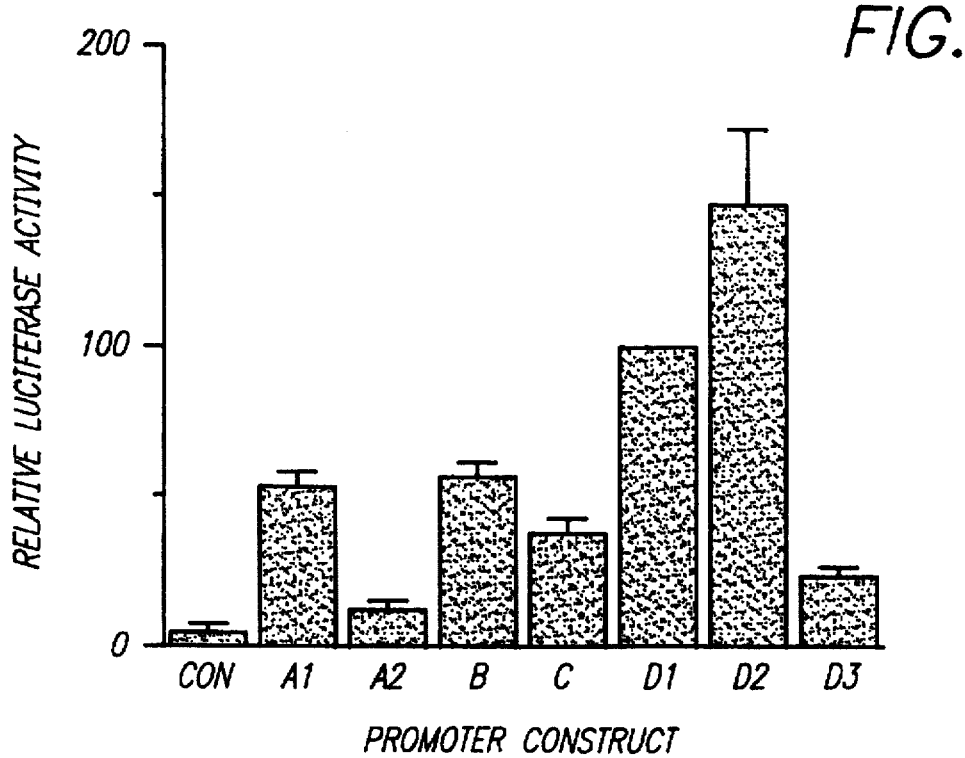

FIG. 4 is a graph showing transcription activity of constructs comprising homologous genomic fragments from the apo(a) 5' region. 5' flanking regions of the genomic fragments were ligated just upstream to the coding region of the luciferase gene, transfected into HepG2 cells and assayed for luciferase activity. Values are the result of 3–5 independent experiments and are presented relative to the activity of the D1 fragment, "Con" is the luciferase plasmid pGENELIGHT-2 without insert. "A1" is the apo(a) genomic fragment derived from an individual with 30 mg/dl plasma apo(a). "A2" is the corresponding fragment from an individual with <1 mg/dl plasma apo(a). "D1", "D2" and "D3" derive from three distinct plasminogen-like 1.2 kb EcoRI genomic fragments isolated from a single individual.

Figure 5:
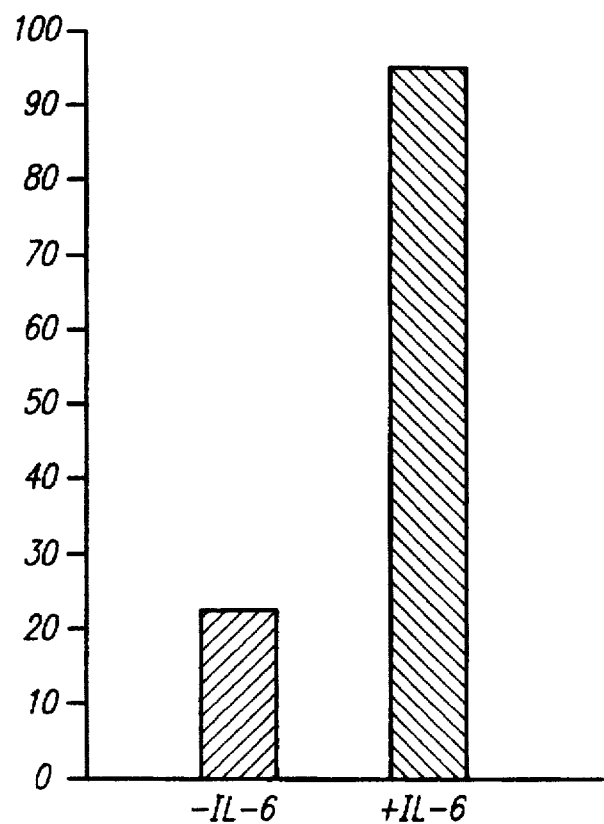

FIG. 5 is a graph showing transcription activity in the presence and absence of added IL-6 in HepG2 hepotocarcinoma cells transfected with plasmid A1 containing the apo(a) gene 5' flanking region from –1442 to –12 inserted into a luciferase reporter construct.

4. SUMMARY OF THE INVENTION

The present invention provides 5'-promoter and regulatory element sequences which control expression of apolipoprotein(a); constructs and vectors comprising apolipoprotein(a) regulatory sequences operatively linked to coding sequences for a heterologous protein, or for an apolipoprotein(a) antisense sequence; oligonucleotide sequences which form triplex complexes with apolipoprotein(a) regulatory sequences; and transgenic animals comprising a heterogenous apolipoprotein(a) regulatory sequence operatively linked to a heterologous protein or to a heterogenous apolipoprotein(a) coding sequence. The invention also provides methods for regulating the expression of apolipoprotein(a); methods for treating elevated serum levels of Lp(a); and methods of screening for compounds capable of modulating the expression of apolipoprotein(a).

5. DESCRIPTION OF THE INVENTION

5.1 Definitions

As applied to an apo(a) regulatory region, "isolated" means an identified nucleotide sequence which is purified to remove regulatory regions from other members of the plasminogen gene family, and which is covalently linked to no more than 10 kb of sequence immediately upstream from the transcription start site of the apo(a) gene. In particular embodiments, isolated sequences may comprise no more than 7, 5, 3, 2, or 1.45 kb of sequence immediately upstream from the transcription start site, as indicated.

As applied to a nucleotide construct comprising an apo(a) regulatory region said to be operatively linked to a coding sequence, "operatively linked" means that the regulatory region is covalently linked 5' to a transcription initiation site, RNA coding sequence, and transcription stop site, whereby said RNA coding sequence is transcribed when the construct is introduced into a suitable cell, such as an hepatocyte or an hepatocarcinoma cell.

As applied to an apo(a) regulatory region operatively linked to a heterologous sequence, "heterologous sequence" means any sequence other than a naturally occurring human genomic DNA sequence coding for apolipoprotein(a). A heterologous sequence includes in one embodiment a sequence coding for a reporter protein, such as luciferase or β-galactosidase. In another embodiment, a heterologous sequence includes a transcribed but untranslated sequence which is antisense to all or a portion of the "sense" sequence coding for human apo(a). In another embodiment, a heterologous sequence includes a sequence coding for human apolipoprotein(a).

As applied to a nucleotide sequence comprising a human apo(a) gene 5'-regulating region greater than 208 bp upstream from the translation start site, the phrase "greater than 208 bp upstream from the translation start site" refers to the portion of the apo(a) regulating region more than 208 bp upstream from the wild-type apo(a) translation start site, whether or not said nucleotide sequence contains the wild-type apo(a) translation start site. The nucleotide sequence optionally may comprise all or part of the apo(a) 5'-regulatory region from –208 to –1 bp.

5.2 Analysis of the Apo(a) 5' Regulatory Sequence

The present invention provides the 5' regulatory region of human apo(a). FIG. 3 (SEQ. ID No. 1)gives the sequence of the 5' regulatory region from –1442 through the ATG translation initiation codon. The sequence from –208 through the ATG has been reported previously, (Ichinose, *Biochem.* (1992) 31:3113–3118) as has the coding sequence for apo(a).

Analysis of the regulatory sequence reveals several significant features. First, at least nine sequences corresponding to known regulatory elements appear within the –208 to –1442 regulatory region. Four of these have the IL-6 response element sequence CTGGGA (Hattori et al., *Proc. Natl. Acad. Sci. USA* (1990) 87:2364). A fifth example occurs beginning at position –55, although the presence of this element was not noted by Ichinose. IL-6 has been shown to promote the synthesis of certain protective plasma proteins (α-cells) "acute-phase proteins") in the liver in response to infections. However, apo(a) was not previously known to be inducible by IL-6.

Another apparent response element which appears in the –208 to –1442 region is the CEBP consensus sequence 1 GCAAT, which occurs beginning at –253 and again beginning at –911. This latter occurrence is in close proximity to an single nucleotide change at –913 occurring on an allelic variant which has been shown to express apo(a) at low levels. This observation supports the inference that this CEBP response element is active in regulatory expression of apo(a).

The reverse complementary sequence to the CEBP response element (denoted CEBP-RC in FIG. 4) occurs at –195. The presence of this sequence was not noted by Ichinose.

A third apparent response element occurring in the –208 to –1442 region is for LF-AI, consisting of the heptanucleotide TGAGCCA beginning at position –1225. Of some interest is the occurrence of this sequence only 15 bp 3' to the beginning of an IL-6 response element. The 22 nucleotide sequence (contained in SEQ. ID NO: 1) containing both response elements.

CTGGGATTACAGAGTTGAGCCA (NUCLEOTIDES 303–324 OF SEQ. ID NO:1) provides a unique target for oligonucleotide therapeutics intended to regulate the expression of apo (a).

An alternate form of the LF-AI sequence, TGAACC, occurs beginning at nucleotide –147. Here also, the presence of this response element was not noted by Ichinose.

Another striking sequence motif which occurs beginning at –1411: the pentanucleotide TTTTA is repeated eight times in tandem. Notably, the allelic variant which expresses low levels of apo(a) has a ninth repeat of the motif. The extra tandem repeat apparently coincides with the presence of the mutation at position –914 observed in the low-expression allele given in the A2 construct.

5.3 Antisense Constructs

An embodiment of the present invention provides an apo(a) 5'-regulatory region comprising a region greater than 208 pb upstream of the human apo(a) translation start site, operatively linked to a sequence which is antisense to a transcribed sequence of an apo(a) gene. The antisense sequence is sufficiently long (greater than 15 bp) to bond selectively to mRNA transcribed from the wild-type apo(a) gene. Preferably such antisense sequence corresponds to a region at the 5'-end of the translated mRNA sequence; however, due to the high level of homology with plasminogen at the leader sequence, the preferred antisense target will be outside the leader sequence domain. Preferred antisense targets are regions of maximal sequence difference between apo(a) and plasminogen.

The antisense constructs may be inserted into hepatotrophic vectors, or may be used without vector sequences. The constructs are used to transfect liver cells. Transfected cells transcribe both the natural apo(a) mRNA and the antisense oligonucleotide. The two sequences duplex, thereby inhibiting expression of apo(a) protein.

The antisense construct may be targeted to hepotocytes using a hepotrophic virus vector, such as hepatitis virus. Alternatively, the antisense construct may be incorporated within or linked to a liposome having a protein component which is targeted to a hepatocellular receptor, such as apoB and the LDL receptor.

The antisense constructs and vectors may be used to transfect cells in vitro or administered to a person to downregulate apo(a) expression.

5.4 Triplex Oligonucleotides

Triplex oligonucleotides provide another means for downregulating apo(a) expression. Rules for devising a triplex-forming oligonucleotide have been devised; see Chastain et al, *Nucleic Acids Res.* (1991) 20:315–18; Orson et al, id. (1991) 19:3435–41; Beal et al, *Science* (1991) 251:1360–63; Maher et al, *Science* (1989) 245:725–30. In general, the triplex-forming oligonucleotide has the sequence correspondence:

oligo 3'—T G G T
duplex 5'—A G C T
duplex 3'—T C G A

Thus for any given sequence in the apo(a) regulatory region upstream from position –208, a triplex forming sequence may be devised.

Triplex-forming oligonucleotides preferably are at least 20, more prefereably 25, still more preferably 30 or more nucleotides in length, up to 50 or 100 bp.

The triplex-forming DNA may have a variant structure to limit degradation, such as a 3' amine termination site.

Targets preferably include at least one region containing a regulatory element and adjacent sequence. A particular target of interest is the region comprising IL-6 and LF-AI response elements at –918 to –940. Another target includes position –913 and the proximal CEBP regulatory element.

6. MATERIALS AND METHODS

6.1 Cloning of 5' Flanking Region of the Apo(a) gene and Related Members of the Plasminogen Gene Family Electrophoresis, blot hybridization and other standard molecular biology procedures essentially followed the protocols of Sambrook, Fritsch and Maniatis. Genomic libraries in bacteriophage lambda (LAMBDA-ZAP 11 and GIGA-PACK GOLD 11; Stratagene) were constructed from human genomic DNA digested to completion with Eco RI and screened with the probe pcr A (see below). In some cases, the Eco RI digested DNA was size-selected by fractionation by 1% agarose gel electrophoresis. Positive clones were isolated as pBLUESCRIPT plasmids by the in vivo excision procedures detailed by the manufacturer, and sequenced to completion by the Sanger di-deoxy method using the SEQUENASE kit (United States Biochemical Corporation) and oligonucleotide primers derived either from vector sequences, or from previous sequence analysis of the cloned inserts. In some cases, nested deletion sets were produced by the exo III mung bean system (Stratagene).

6.2 Oligonucleotide Primer Sequences

Primer sequences (pcr 6) (SEQ. ID NO:2) GCCTGTTG-GAAAGCTTG and (pcr 7) (SEQ. ID NO:3) AGTAGAA-GAACCACTTC were used to generate the genomic DNA 483 by probe designated PCR-A. ACCACATGGCTTTGC (SEQ. ID NO:2) the reverse complement of sequence in the first kringle region of apo(a) mRNA, was used to determine the mRNA start site by reverse transcriptase extension. Human liver poly (A+) RNA was isolated by the guanidium isothiocyanate procedure.

6.3 Luciferase Reporter Gene Constructs

In order to assay promoter activity, a series of reporter gene constructs was synthesized (pLuc A-D), comprising the 5' flanking regions of the apo(a) gene and its homologues inserted into the polylinker region of pGENELIGHT-2 (Promega Inc., Wisc.), a promoterless vector containing the firefly luciferase gene. The genomic inserts were isolated from modified pBLUESCRIPT plasmids of the original clones from which genomic fragments 3' to the desired flanking regions had been removed by restriction enzyme digestion. The flanking region inserts were isolated from these modified plasmids by digestion with restriction enzymes appropriate for directional ligation into the pGENELIGHT-2 poly-linker. The inserts contained 1.4 kb of DNA upstream of a Bal I site located 12 nucleotides before the translation initiation ATG for the A1, A2 and B fragments, 1.07 kb upstream of this site in the D fragments, and 3.0 kb upstream of a Hinc II site at –54 bp for the C fragment.

The insert for plasmid pLucA1 was isolated using an intermediate plasmid constructed from a Cla1-Ball digest of the original Bluescript plasmid containing the 4.8 kb A1 insert. The resulting Bluescript vector containing 1.4 kb of 5' flanking region of the 4.8 kb insert terminating at a Bal1 site –12 bp from the ATG, was gel-isolated, the Cla1 cohesive end blunted by Klenow extension, and self-ligated. Digestion of this plasmid with Sac1-Xho1 produced an insert containing 1.4 kb of 5' flanking region of the 4.8 kb which was cloned into Sac1-Xho1-digested GeneLight 2 plasmid. Plasmid pLucA2 was constructed from an intermediate plasmid obtained by Bal1-Smal digestion of the Bluescript plasmid containing the 4.8 kb A2 insert. The resulting fragment containing the vector and 1.4 kb 5'flanking region of the A2 insert, terminating at the Bal2 site terminating at –12 bp from the ATG, was blunt end ligated and the 1.4 kb fragment excised by Kpn1-Spe1 digestion and cloned into the Kpn1-Nhe1-digested gene-light 2 plasmid. Plasmid pLucB was constructed with an insert derived from Spe1-Ball digestion of the Bluescript plasmid containing the 3.6 kp B insert. The resulting vector insert fragment containing 1.4 kp 5' flanking sequence of clone B, terminating at the Bal site –12 from the ATG was gel-isolated, the Spe1 cohesive end blunted with Klenow enzyme and the construct self-ligated. A fragment containing 1.4 kb of 5' flanking sequence was excised from this plasmid by XbaI-EcoR V digestion and ligated into SmaI-NheI sites of the GeneLight 2 plasmid polylinker. Plasmid pLuc C was constructed from an intermediate plasmid produced by HincII digestion of the Bluescript plasmid containing the 3.2 kb C clone. This excises a 200 bp fragment leaving a vector insert fragment containing 3 kb of 5' flanking region of the 3.2 clone terminating at a HincII site −54 bp from the ATG. After religation of the plasmid, the 3 kb 5' flanking region was excised by SacI-XhoI digestion, and separated from the 3 kb Bluescript vector by gel-isolation, following digestion with ScaI, which cuts the vector into 1 kb and 1.8 kb fragments, and cloned into the SacI-XhoI-digested GeneLight 2 plasmid. pLuc D1 and D2 were constructed from intermediate plasmids produced by BaI-SmaI digestion of the Bluescript plasmids containing these inserts followed by gel-isolation and self-ligation of the resulting vector-insert fragment containing approximately 1 kb of 5'flanking sequence terminating at the BaI site at −12 bp from the ATG. The 5' flanking insert was excised by SacI-KpnI digestion and cloned into SacI-KpnI digested GeneLight 2 vector. pLucD3 was constructed from an intermediate plasmid produced by digestion of the Bluescript D3 clone with Hinc2, followed by gel-isolation of the 4 kb vector insert fragment and self-ligation resulting in a fragment containing 1 kb of 5' flanking region of D3 terminating at the Hinc2 site at −54 bp from the ATG. This fragment was excised by XhoI-SacI digestion and cloned into these sites in the GeneLight2 vector.

6.4 Transfection and Assay of Reporter Gene Constructs

Plasmids for transfection were purified by two cesium chloride density gradient ultracentrifugations or by QIAGEN columns (Qiagen Inc., Calif.). For transient transfections with luciferase construct plasmids, HepG2 cells were seeded at $0.75 \times 10^8$ cells per 6 cm dish and maintained in DMEM (Gibco-BRL) medium supplemented with 10% FCS. Transfections were performed when the cells attained 40–60% confluence. For each dish, 10 µg of test plasmid DNA and 5 µg of pSV-β-galactosidase control plasmid (Promega Inc., Wisc.) were mixed with 1.5 ml of Opti-Mem medium (Gibco-BRL) in a polystyrene tube and 1.5 ml of Opti-Mem containing 30 µg of Lipofectin (Gibco-BRL) was added. Complexes were allowed to form for 30 mins. at room temperature and the lipofectin-DNA mix was added to the dishes after washing the monolayers three times in Pucks Saline A (Gibco-BRL). After 16 hours the medium was replaced by 5 ml of DMEM containing 10% FCS, and incubation continued for 48 hours before assay of cellular luciferase and β-galactosidase activity.

Monolayers were washed five times with ice-cold phosphate-buffered saline (PBS), scraped in 1 ml PBS and pelleted by centrifugation at 4° C. for 10 seconds in a microfuge. The pellet was resuspended in 100 µl of 0.1M $KH_2PO_4$ buffer, pH7.8, 1mM DTT, and lysed by three freeze-thaw cycles with vigorous vortexing between each cycle. Lysates were stored in aliquots at −70° C. if not assayed immediately. Luciferase activity was measured by mixing 100 µl of luciferase substrate solution (Promega Inc.) with 20 µl of cell lysate and a 0–10 second integral read in a Monolight 2001 luminometer (Analytical Luminescence Laboratories). β-Galactosidase activity was measured after dilution of the lysates one in one hundred in $KPO_4$ buffer. Diluted lysate (20 µl) was incubated for one hour at room temperature with 200 µl of 10 µg/ml AMPGD chemiluminescent β-galactosidase substrate (Tropix Inc., Mass.) in 0.1M $KPO_4$, 1mM $MgCl_2$ pH 7.8. Light emission was initiated by addition of 300 µl of 1M NaOH containing 10% volume to volume Emerald enhancer (Tropix Inc., Mass.), and a 0–10 second integral read immediately in a luminometer. Luciferase activities were normalized to β-galactosidase activity for each dish. Within each experiment luciferase activity was determined in duplicate dishes, and each plasmid was tested in 3–5 separate experiments; therefore results are expressed as the mean of 6–10 values.

6.5 Construction of Transgenic Mouse

Transgenic mice are produced by injecting fertilized eggs with a construct containing human apo(a) cDNA (isoform $M_r$ 550,000 Da; Kochinsky et al., Biochem. (1991) 30:5044–51) under the regulating control of the human apo(a) regulatory region as given in FIG. 3 (SEQ. ID NO:1. The construct contains 1.44 kb of human apo(a) regulating region upstream of the translation start site, the apo(a) secretion signal sequence. 17 tandem copies of a 342-base pair kringle-4-like domain, a kringle −5 domain, and a protease domain. The 3'-untranslated region of apo(a) is fused to an SV40 early region polyadenylation signal.

This construct is microinjected into fertilized hybrid mouse eggs by the procedure of Brinster et al., Proc. Natl. Acad. Sci. USA (1985) 82:4438–42. The founder transgenic mouse is derived from C57BL/6×SJL F2 eggs and is mated to a C57BL/6×SJL F1 to establish a line. The line is maintained by continued crossing to C57/BL6×SJL hybrids. Control mice are non-transgenic litter mates.

6.6 Evaluation of Atherogenic Effect of Expression of Apo(a) in Transgenic Mice After 6 weeks of age, transgenic mice and non-transgenic siblings are switched from a normal mouse chow diet (Techlad, Madison, Wisc.; 4% mouse/rat chow) to an atherogenic diet containing 1.25% cholesterol, 7.5% saturated fat as cocoa butter, 7.5% casein and 0.5% sodium cholate for approximately 3½ months. At that time, plasma apo(a) is determined by ELISA (GeneScreen, Dallas, Tex.) and total cholesterol by the cholesterol oxidase method. For each animal, four 10 µm sections separated by 50 µm are quantitated. The first and most proximal section to the heart is taken 80 µm distal to the point where the aorta becomes rounded. The area of Oil Red O staining in each section is determined with a calibrated eyepiece, and the mean lesion area per section per animal is calculated for each individual and group of animals. The coded slides are examined blind in two separate analyses by the same examiner.

Lipid and apo(a) accumulation in the aorta of transgenic mice is evaluated by microscopic examination. Low (50×) (a,c) and high (150×) magnification views of adjacent sections of proximal aorta from an apo(a) transgenic mouse fed an atherosclerotic diet are stained for lipid and apo(a).

The heart and attached aorta are fixed in 10% formalin and 10 µm sections prepared. Lipid sections are stained with Oil Red O and hematoxylin, and counterstained with light green. For apo(a) immunostaining, sections are preincubated with 1% rabbit serum for one hour, and subsequently with 1:1000 sheep anti-human Lp(a) antibody absorbed against plasminogen (Immuno, Vienna). This antibody has no appreciable cross reactivity against mouse plasminogen as determined by Western blotting and by immunostaining of control and transgenic mouse liver sections. Bound primary antibody is detected by incubation with biotinylated rabbit anti-sheep IgG at 1:200 followed by quenching of endogenous peroxidase activity with 0.6%

H₂O₂, incubation with avidin biotinylated peroxidase complex, and color production with 3-amino-9-ethyl carbazole following the vendors protocols (Vector Laboratories, Burlingame, Calif.). Control slides are prepared with non-immune sheep serum in place of the primary antibody.

Co-localized apo B and apo(a) immunostaining of transgenic aorta is determined by microscopic examination of adjacent sections of aorta stained for apo(a) or apo B.

The proportions of free and lipid-associated apo(a) from the plasma of transgenic mice on the atherogenic diet is determined. 500 μl of pooled plasma from the three apo(a) transgenic mice on the atherogenic diet was adjusted to d =1.215 g/ml with KBr and centrifuged. After adjusting to equal volumes, aliquots of the top and bottom fractions are electrophoresed on a 6% SDS polyacrylamide gel under reducing conditions, transferred to nitrocellulose, and probed with sheep anti-human apo(a) (Immuno, Vienna) at 1:400, followed with peroxidase-conjugated anti-goat IgG at 1:400 and color development with 4-chloro-1-naphthol. The ratio of apo(a) in dilutions of the bottom (lipid free) and top fractions is used to estimate the proportion of the plasma apo(a) is lipid associated.

7. RESULTS

7.1 Identification of Six Closely Related Genes/ Gene Fragments cDNA sequence analysis had shown that the 5' ends of human apo(a) and plasminogen mRNA are nearly identical. Initial hybridization of human genomic DNA Southern blots with fragments from the 5' region of the human apo(a) cDNA indicated the existence of several distinct genomic homologues of this region. A 483 bp probe (designated pcr A) covering this region was synthesized by PCR from genomic DNA, based upon plasminogen gene sequence of Peterson et al. (Peterson, T. E., Martzen, M. R., Ichinose, A. and Davie, E. W. (1990) *J. Biol. Chem.* 265, 1604–6111). When hybridized to an EcoRI digest of human DNA at high stringency, the pcr A probe detects four fragments designated A(4.8 kb), B(3.6 kb), C(3.1 kb), and D(1.2 kb) (FIG. 1 insert). The intensity of the D fragment indicated that it might contain two or more copies. Several clones corresponding to each of these hybridizing genomic fragments were isolated from EcoRI complete digest lambda libraries and sequenced to completion. Sequence analysis confirmed the existence of more than four extremely homologous fragments of the genome, since 3 variants of the 1.2 kb fragment were isolated from one individual (FIG. 1). Comparing the sequence of the cloned genomic fragments to the published cDNA sequence of human apo(a) and plasminogen (Sambrook, J., FFritsch, E. and Maniatis, T. Molecular Cloning, 2nd ed., New York: Cold Spring Harbor Laboratory Press, 1989, Malinowski, D. P., Sadler, J. E., and Davie, E. W. (1984) *Biochemistry* 23, 4243–4250, Forsgrent, M., Raden B., Isnaelsson, M., Larsson, K., and Heden, L. P. (1987) *FEBS Lett.* 213, 254–260), we found that all four fragments contain a region of over 95% sequence identity which encompasses the translation initiation codon and first exon of these genes, and contains the identical sequence CAG/GTA at the first splice donor site (The first exon of both the human plasminogen and apo(a) genes ends at an identical location 49 nucleotides following the ATG, and codes for the first 16 amino acids of the signal peptide sequence.) The 4798 bp of our A fragment sequence contain an exact match with the 400 bp sequence of apo(a) I given by Ichinose (Ichinose, A. (1992) *Biochemistry* 31, 3113–3118), and but one mismatch (at –21 bp before the ATG) with the overlapping region of apo(a) mRNA reported by McLean et al. (McLean, J., Tomlinson, J., Kuang. W., Eaton, D., Chen, E., Fless, G., Scanu, A., Lawn, R. (1987) *Nature* 330, 132–137). The assignment of the A fragment to the bona fide apo(a) is consistent with the recovery of overlapping lambda genomic clones which contain the A fragment sequence with clones encoding kringle regions of apo(a). The transcription start site of apo(a) mRNA was determined by primer extension with reverse transcriptase (FIG. 2). The major start site appears to occur at 141 bases before the translation start ATG. This is twenty bases farther downstream than the transcription start site reported for human plasminogen mRNA by Malgaretti et al. (Malgaretti, N., Bruno, L., Pontoglio, N., Candiani, G., Meroni, G., Ottolenghi, S., and Taramelli, R. (1990) *Biochem. Biophys. Res. Comm.* 173, 1013–1018). The sequence of the 5' region of the human apo(a) gene is given in FIG. 3 (SEQ. ID NO:1).

7.2 Promoter Activity of Genomic Fragments

To begin analysis of elements that control transcription of the apo(a) gene,and to determine which of the other promoter fragments are functional, the cloned genomic fragments were inserted into luciferase reporter plasmids. Genomic DNA from the 5'Eco RI site of each fragment to a point in the 5'untranslated region was inserted into the GeneLight-2 plasmid (Promega) upstream of the firefly luciferase gene (see Methods). The recombinant plasmids contained 1.4 kb of A fragment 5' untranslated sequence, 1.2 kb of B fragment sequence, 3 kb of C fragment sequence and 1.1 kb of D fragment sequence. All of the fragments proved competent to drive transcription of the reporter gene following transfection into HepG2 hepatocarcinoma cells (FIG. 4), suggesting that more than just plasminogen and apo(a) genes might be transcribed from this gene family (see Discussion). Apo(a) gene A fragments were cloned and tested from two individuals. A1 derived from an individual with relatively high plasma Lp(a) concentration (30 mg/ml), while A2 derived from an individual with Lp(a) below the level of detection by ELISA and by Northern blot hybridization. The only DNA differences in the two A fragments are a single base substitution 913 nucleotides before the ATG and nine, rather than eight copies of the repeated sequence TTTTA at position –1373 (see FIG. 3). When normalized to a value of 100% for the D1 fragment, the promoter activity of A1 was 53%, while A2 was only 11%, which is consistent with the lower plasma apo(a) concentration in the A2 individual. In addition, fragment B had 57% relative promoter activity, fragment C had 38%, D2 had 149% and D3 had 23%.

All publications mentioned herein are incorporated by reference to the same extent as though incorporated individually.

What is claimed is:

1. A nucleotide sequence comprising the human apolipoprotein(a) gene 5'-regulatory region from nucleotide position −208 to nucleotide position −1442 of FIG. 3 nucleotides 1–1235 of SEQ ID NO: 1), operatively linked to a heterologous sequence.

2. The nucleotide sequence of claim 1 wherein said apo(a) gene 5'-regulatory region is derived from a human subject having serum Lp(a) levels of greater than 5 mg/mL.

3. The nucleotide sequence of claim 1 wherein said apo(a) gene 5' regulatory region is derived from a human subject having serum Lp(a) levels of less than 5 mg/ml.

4. The nucleotide sequence of claim 1 wherein the heterologous sequence codes for a heterologous polypeptide.

5. The nucleotide sequence of claim 4 wherein said heterologous polypeptide is an enzyme.

6. The nucleotide sequence of claim 5 wherein said enzyme is β-galactosidase.

7. The nucleotide sequence of claim 5 wherein said enzyme is luciferase.

8. The nucleotide sequence of claim 5 wherein said enzyme is chloramphenicol acetyl transferase (CAT).

9. The nucleotide sequence of claim 4 wherein said heterologous polypeptide is avidin.

10. The nucleotide sequence of claim 4 wherein said heterologous polypeptide is an immunogen.

11. A nucleotide sequence comprising a human apolipoprotein(a) gene 5'-regulatory region operatively linked to a heterologous sequence, said 5'-regulatory region comprising at least one hundred consecutive nucleotides of the regulatory region depicted in FIG. 3 from nucleotide position −208 to −1442 nucleotides 1–1235 of SEQ ID NO: 1).

12. A vector comprising the human apolipoprotein(a) gene 5'-regulatory region from nucleotide position −208 to −1442 of FIG. 3 nucleotides 1–1235 of SEQ ID NO: 1), operatively linked to a heterologous sequence.

13. The vector of claim 12 wherein the apo(a) gene 5'-regulatory region comprises an IL-6 responsive element.

14. The vector of claim 12 wherein said IL-6 responsive element comprises the sequence CTGGGA.

15. The vector of claim 12 further comprising an HNF-1α responsive element.

16. The vector of claim 12 wherein the heterologous sequence codes for a polypeptide.

17. The vector of claim 16 wherein said polypeptide is an enzyme.

18. The vector of claim 17 wherein the enzyme is luciferase.

19. An isolated nucleotide sequence comprising at least thirty consecutive nucleotides (1) from the human apolipoprotein(a) gene 5'-regulatory region depicted in FIG. 3 from nucleotide position −208 to −1442 nucleotides 1–1235 of SEQ ID NO: 1) or (2) from the complement of said 5'-regulatory region.

20. A nucleotide sequence comprising at least fifteen nucleotides capable of forming a triplex DNA complex with a double stranded DNA comprising the human apolipoprotein(a) gene 5'-regulatory region depicted in FIG. 3 from nucleotide position −90 to −1442 nucleotides 1–1353 of SEQ ID NO: 1).

21. The nucleotide sequence of claim 20 wherein said triplex DNA complex is formed with an IL-6 responsive element.

22. The nucleotide sequence of claim 20 wherein said triplex DNA complex is formed at a site comprising nucleotide −913 (nucleotide 529 of SEQ ID NO:1).

23. The nucleotide sequence of claim 20 wherein said triplex DNA complex is formed at a site comprising the sequence TTTTA.

24. A transfected mammalian cell containing the nucleotide sequence of claim 5, or progeny of said transfected cell.

25. The nucleotide sequence of claim 11 wherein said apolipoprotein(a) gene 5'-regulatory region comprises an IL-6 responsive element.

26. The nucleotide sequence of claim 25 wherein said IL-6 responsive element comprises the sequence CTGGGA.

27. The nucleotide sequence of claim 11 wherein said apolipoprotein(a) gene 5'-regulatory region comprises a HNF-1α responsive element.

28. The nucleotide sequence of claim 11 wherein said apolipoprotein (a) gene 5'-regulatory region comprises an CEBP responsive element.

29. The nucleotide sequence of claim 28 wherein said CEBP responsive element comprises the sequence GCAAT.

30. The nucleotide sequence of claim 11 wherein said apolipoprotein(a) gene 5'-regulatory region comprises a LF-AI responsive element.

31. The nucleotide sequence of claim 30, wherein said LF-AI responsive element comprises the nucleotide sequence CTGGGATTACAGAGTTGAGCCA (nucleotides 303–324 of SEQ ID NO: 1).

32. The nucleotide sequence of claim 30, wherein said LF-AI responsive element comprises the sequence TGAGCCA.

33. The nucleotide sequence of claim 11 wherein said apolipoprotein(a) gene 5'-regulatory region comprises an IL-6RC responsive element.

34. The nucleotide sequence of claim 33, wherein said IL-6RC responsive element comprises the sequence CTTTCACCA.

35. The nucleotide sequence of claim 11 wherein the heterologous sequence codes for a heterologous polypeptide.

36. A vector comprising a human apolipoprotein (a) gene 5'-regulatory region operatively linked to a heterologous sequence, said 5'-regulatory region comprising at least one hundred consecutive nucleotides of the regulatory region depicted in FIG. 3 from nucleotide position −208 to −1442 nucleotides 1–1235 of SEQ ID NO: 1).

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 2542 base pairs
        ( B ) TYPE: nucleic acid
        ( C ) STRANDEDNESS: double
        ( D ) TOPOLOGY: unknown ( i i ) MOLECULE TYPE: DNA (genomic)

( x i ) SEQUENCE DESCRIPTION: SEQ ID NO:1:

```
GAATTCATTT GCGGAAAGAT TGATACTATG CTTTTATTTT ATTTTATTTT ATTTTATTTT      60
ATTTTATTTT ATTGAGACTC TCACCCCGGT TGAAGTGCAC TGACGTGATT TTGGCTCACT     120
GCAACTTCCA CCTCCTGGGT TCAAGTGAAT ACTCCAGCCT CCCTAGTAGC TGGGATTACA     180
GGTGCCCACC ACCACGCCTG GCTAATTTTT GTATTTTAG  TAGAGATGGG GTTTCACCAC     240
ATTGGCCTGG CTGGTCTCAA ACTCCTGACC TTGTGATCCA CCTGTCTTGG CCTCCCAAAG     300
TGCTGGGATT ACAGAGTTGA GCCACCGCAC TCGACCCTAT GTTTTATTTT TAAAAATATT     360
TATTTATTTA TTTAAGCCAC AACTACTAGA ATAGGAAGGA TTGATATTTT ATTAATTTTA     420
TTTGGTATTT ATTATTTTTT TTTCTTTCCT GAGACATTCT TGCTCTGTCA CCCAGGCTGG     480
AGTGCAGTGG CACATTCTTG GCTCACTGCA ACCTCCATCT CCTGTGTTCG AGCAATTCTA     540
GTGCCTCAGC CTACTTAGTA GCTGGGATGA CTGGCATGTG CCTCCACACC AGCTAATTT     600
TTGTATTTTT TGTAGAGACA GGGTTTTGGC ATGTTGCCAG GCTTGTCTCA AACTCCTGGC     660
CTCAGGTGAT CCATCTGCCG TGGCCTCCCA AAATGCTGGG ATTATAGGCA TGAGCCACCA     720
CCCCCTCCTG GAAGGATTGA TATCTTATAA CATAATTTAT AATTACAGAA AACATGTGAG     780
TTCACTAGGA ATAAATAAAT TTGAAGATA  ATAAAAGATT TTCACTTATG TTGTCATTTC     840
GGCACAGTTT GGTATAGGAT GTGGAGATGT TAACATTTAT ACCTAGCTTG CTCGTAAACT     900
AAGACCTGAA AGGGTTGTGT CTATCAGCTG CACCCCTGGG TAGCGACACA ACCTCGGGAA     960
GGCCTCAGCC CCCTCCTCGT ACAGCACTGC CTGTTGGAAA GCTTGAGGGA GGCTATGGAT    1020
GTGCAGCACT TGGCAGAGGG TCTGGTCATG GAAGTTACCA GCAAATATGA GCTACTTTTA    1080
TGATTTTATT TTATCCAAAA GAAAGAGAAT GAAAGAAGAG GGGAGGAAAC AAGACTAATC    1140
AGGAAAGATG AAGGTCTAGG GGTGAGGGAA GGAGTAAGGA GACATAAAGG CAATGTGGAG    1200
CAGCTGAGGG GGGAAATGGC TTTCACCACT TCCAGCATC  TATTGACATT GCACTCTCAA    1260
ATATTTTATA AGACTCTATA TTCAAGGTAA TGTTTGAACC TGCTGAGCC  AGTGGCATGG    1320
GTCTCTGAGA GAATCATTAA CTTAATTTGA CTATCTGGTT TGTGGGTGCG TTTACTCTCA    1380
TGTAAGTCAA CAACGTCCTG GGATTGGGAC ACACTTTCTG GGCACTGCTG GCCAGTCCCA    1440
AAATGGAACA TAAGGAAGTG GTTCTTCTAC TTCTTTTATT TCTGAAATCA GGTAAGACAT    1500
AGTTTTTTTA AATTATAAGA ATTATTTTTT CTCCACAAT  GTAGTAAAAA TACATATGCC    1560
ATGGCTTTAT GTGCAATTCA TTTAATTTTT GATTCATGAA ATTCCAGTT  CAAATCTTG     1620
TATATGATTG AAAAATTCTT CCAAAAATTA GTTTAATTTC CCCGTGAAGA CTGTCACGGT    1680
GCTGGAATGA ATGGGCAGAA AAAATAATGG TTGATTTTTC TAATCTAAAA GAGTGTGCCT    1740
ACATGATGGC CAGTCTGGCT GAAAAATAAA TAGCCATTGT AGCTAACTAT GCAAAGGATG    1800
```

-continued

```
GCTAAGCTCT TCGCTTGGTT CTCAGTTTCA TTAATTTATA TCATCTCTGT TCAGGTGCCA    1860
TGCTCCCCTC ACTAGCAAGT TGAAACAATG AAATAACTCT TTGAATATGT TTGGTTCCTT    1920
GACCTGTTCA TGGAGTGGGA CTCAGCATTT CTCTCTTTGT TATGGCCTGA GTAAGGCTTT    1980
CCATCGGTAT ACATTTGCTT CTTATCCCTG GAGAAATTAT ACACATCCAT TTGCCAGATG    2040
ATATACACAT ATAATGATTC AACAAATACT CAGGGTATTT GTTGAGTGGG TTAGGTCCCC    2100
ACATTTTTAT ACATACATAC ACACATACAC ACCGTGTGTG ATTGTGAATG TAAGTGTGTG    2160
TCCTTTACAA ATACTAGCTT ATTTAGCTCA TGGTATAGGT AGGGTAGCAT AGTCATCCCC    2220
ATTTTATAAA CAAAGAAATC TAGACTTAGG AAAATCATGT TATTTGTCTC GTGACCAAAT    2280
TCCCAAATCA AGGAAATAAA GAAACCTGGA TTTAAGCCAG ATTTCCAAGA AAAAATCTAG    2340
GGCTCTTCTC ACTTTTTCAT CTTTGTTCCA ACATTTGAAA AAATAAATCT AAACACATTC    2400
CAATGTAACT GAAGAGCAGG TTAATTGTTT GCCACTTGCA GAATCCAATT AAGAAGAGAG    2460
AAGTCTGGTA TAAAGAAAGT GATTTGCTTC CAAAGCTAGC TTAGGGGAAG AAATGCAGCA    2520
GTCCTGCCGT ACCACTTCAC TT                                              2542
```

( 2 ) INFORMATION FOR SEQ ID NO:2:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:2:

```
GCCTGTTGGA AAGCTTG                                                      17
```

( 2 ) INFORMATION FOR SEQ ID NO:3:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:3:

```
AGTAGAAGAA CCACTTC                                                      17
```

( 2 ) INFORMATION FOR SEQ ID NO:4:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:4:

```
ACCACATGGC TTTGC                                                        15
```